US00RE39075E

(19) United States
(12) Reissued Patent
Verkaart

(10) Patent Number: US RE39,075 E
(45) Date of Reissued Patent: Apr. 18, 2006

(54) HEATER FOR PHYSIOLOGICAL FLUIDS

(75) Inventor: Wesley H. Verkaart, Duxbury, MA (US)

(73) Assignee: Smiths Medical ASD, Inc., Rockland, MA (US)

(21) Appl. No.: 10/032,559

(22) Filed: Jan. 2, 2002

Related U.S. Patent Documents

Reissue of:
(64) Patent No.: 4,759,749
Issued: Jul. 26, 1988
Appl. No.: 06/866,910
Filed: May 27, 1986

U.S. Applications:

(63) Continuation of application No. 08/758,853, filed on Dec. 2, 1996, now abandoned, which is a continuation of application No. 08/571,706, filed on Dec. 6, 1995, now abandoned, which is a continuation of application No. 08/145,099, filed on Nov. 3, 1993, now abandoned, which is a continuation of application No. 07/979,434, filed on Nov. 20, 1992, now abandoned, which is a continuation of application No. 07/558,177, filed on Jul. 26, 1990, now abandoned.

(51) Int. Cl.
*A61F 7/12* (2006.01)

(52) U.S. Cl. ..... 604/113; 604/6.13; 604/6.11; 604/151; 165/67; 165/156; 422/46

(58) Field of Classification Search ..... 604/4.01, 604/80, 82, 113, 114, 259, 322, 508, 6.11, 604/6.13, 151, 131; 128/DIG. 3; 607/96, 607/104; 165/67, 68, 154, 156; 285/231, 285/345; 422/46
See application file for complete search history.

(56) References Cited

U.S. PATENT DOCUMENTS 1,873,590 A * 8/1932 James ..... 285/345
2,432,592 A * 12/1947 Stecher et al. ..... 285/231
2,910,981 A * 11/1959 Wilson et al. ..... 604/114
3,064,649 A * 11/1962 Fuson ..... 128/400
3,374,066 A * 3/1968 Farrant ..... 604/113
3,643,733 A * 2/1972 Hall et al. ..... 165/154
3,831,672 A * 8/1974 Battisti ..... 165/156
4,066,119 A * 1/1978 Stedman ..... 165/67
4,354,548 A 10/1982 Carlsson
4,437,513 A * 3/1984 Castiglioni et al. ..... 165/154
4,475,584 A * 10/1984 Martin et al. ..... 165/154
4,559,999 A * 12/1985 Servas et al. ..... 165/156
4,562,890 A * 1/1986 Matoba ..... 165/156
4,623,333 A * 11/1986 Fried ..... 604/113
4,678,460 A * 7/1987 Rosner ..... 604/80

FOREIGN PATENT DOCUMENTS

DE 3443085 A1 * 11/1984
EP 0 108 525 * 5/1984

* cited by examiner

*Primary Examiner*—Brian L. Casler
*Assistant Examiner*—Cris L. Rodriguez
(74) *Attorney, Agent, or Firm*—Louis Woo

(57) ABSTRACT

A self-contained portable unit for heating physiological fluids is disclosed. A heat exchanger is disposable to ensure sterility, and the hot exchanger is attached to a heating system by inserting it between opposed fluid connection elements. One of the fluid connection elements is movable to permit the heat exchanger to be installed and removed easily by inserting one end of the heat exchanger in one of the fluid connection units and moving the other fluid connection unit into contact with an opposite end of the heat exchanges. The heating fluid is heated by an electric heating element and is circulated by an electric pump.

20 Claims, 5 Drawing Sheets

FIG. 2
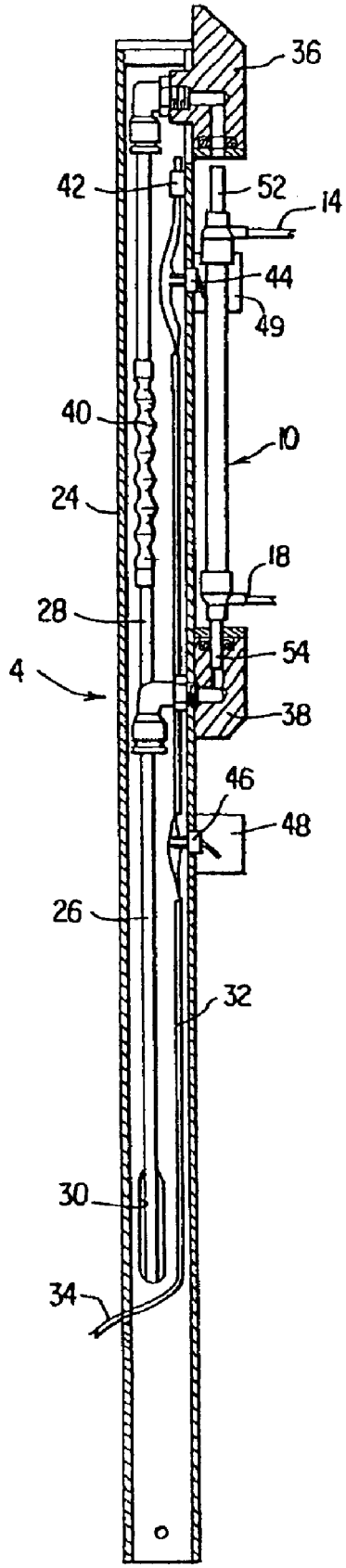
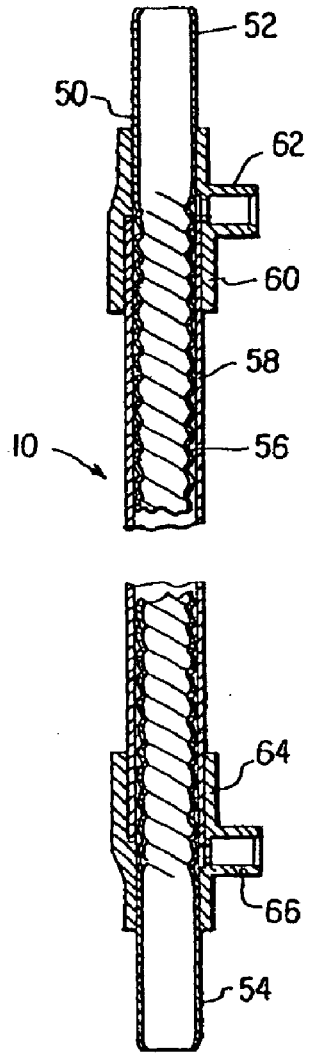
FIG. 3

HEATER FOR PHYSIOLOGICAL FLUIDS

Matter enclosed in heavy brackets [ ] appears in the original patent but forms no part of this reissue specification; matter printed in italics indicates the additions made by reissue.

*This application is a continuation of application No. 08/758,853 filed Dec. 2, 1996, since abandoned, which is a continuation of application No. 08/571,706 filed Dec. 6, 1995, since abandoned, which is a continuation of application No. 08/145,099 filed Nov. 3, 1993, since abandoned, which is a continuation of application No. 07/979,434 filed Nov. 20, 1992, since abandoned, which is a continuation of application No. 07/558,177 filed Jul. 26, 1990, since abandoned, which is a reissue of application No. 06/866,910 filed May 27, 1986, U.S. Pat. No. 4,759,749.*

FIELD OF THE INVENTION

This invention relates to the art of devices used with physiological fluids. In particular, the invention is an apparatus for heating a physiological fluid before introduction into a patient.

BACKGROUND ART

In many medical procedures, it is necessary that fluids to be administered to a patient be heated. For example, whole blood and packed cells are stored in refrigerators at a temperature of approximately 4° C. These fluids often are required to be administered to a patient within a short period of time, which necessitates warming them to a temperature approximately equal to that of the patient, i.e. 37° C.

Great care must be exercised when heating fluids such as whole blood or packed cells to avoid damaging the cells. For example, it is generally accepted that whole blood and packed cells should not be exposed to a temperature above 44° C. This places a severe restriction on the techniques used to heat quickly fluids which have been stored in a refrigerator and which must be administered to a patient within a short period of time.

U.S. Pat. Nos. 3,614,385 (Horstmann), 3,629,552 (Edging), 4,476,867 (Parks), and 4,532,414 (Shah et al.) teach systems for heating blood prior to being administered to a patient. The Horstmann, Edging, and Parks devices use various heat exchangers whereby blood flows through a tube which communicates with a warming fluid in a heat exchanger. It is quite difficult to maintain sterility of the heating apparatus in these systems after the first use because of the complexity of the heat exchangers. The Shah et al. device is simply a heated plate having a groove therein for receiving a tube leading from the bag containing the fluid to be administered.

U.S. Pat. No. 2,910,981 (Wilson et at.) shows a device for conducting blood transfusions. A heat exchanger is in fluid communication with a heating element, and the blood to be ministered passes through the heat ex. changer before being administered to the patient. The heat exchanger comprises a central tube surrounded by an outer tube, and the heating fluid passes through the space between the inner and outer tubes. The heat ex. changer is threadedly connected to valves at opposite ends. No structure is described for supporting the various elements described in the patent.

SUMMARY OF THE INVENTION

The invention is a self-contained, free standing system which permits controlled, but rapid heating of cellular fluids as they are being administered to a patient. The heating of the cellular fluids is controlled to prevent damage to the fluids from various causes including overheating.

The system comprises two major parts. A first part includes a heating element, a support pole, and a wheeled base. A second part comprises a heat exchanger and, optionally, a filter. The heat exchanger and filter are disposable and are removably attached to the support pole. The heat exchanger is disposable to facilitate each patient's use of a new, sterile heat exchanger.

The heat exchanger is easily installed on the pole, which includes a fixed mounting block and a movable mounting block. Opposite ends of the heat exchanger comprise nipples which are received in O-ring containing recesses in the mounting blocks. Thus, installation and removal of the disposable heat exchanger are quite easy.

The system may also include a filter which would be attached to an outlet of the heat exchanger. Sensors on the pole detect when the heat exchanger or the filter is in a correct place to control operation of the heating system. The heating system comprises a tank and a heating element in the outlet line of the tank. A pump circulates a heating fluid from the tank and heating element through the disposable heat exchanger.

BRIEF DESCRIPTION OF THE DRAWINGS

FIG. 2 is a longitudinal cross-section of the support pole.

FIG. 3 is a longitudinal cross-section of the heat exchanger.

DETAILED DESCRIPTION OF THE INVENTION

Figure 1:
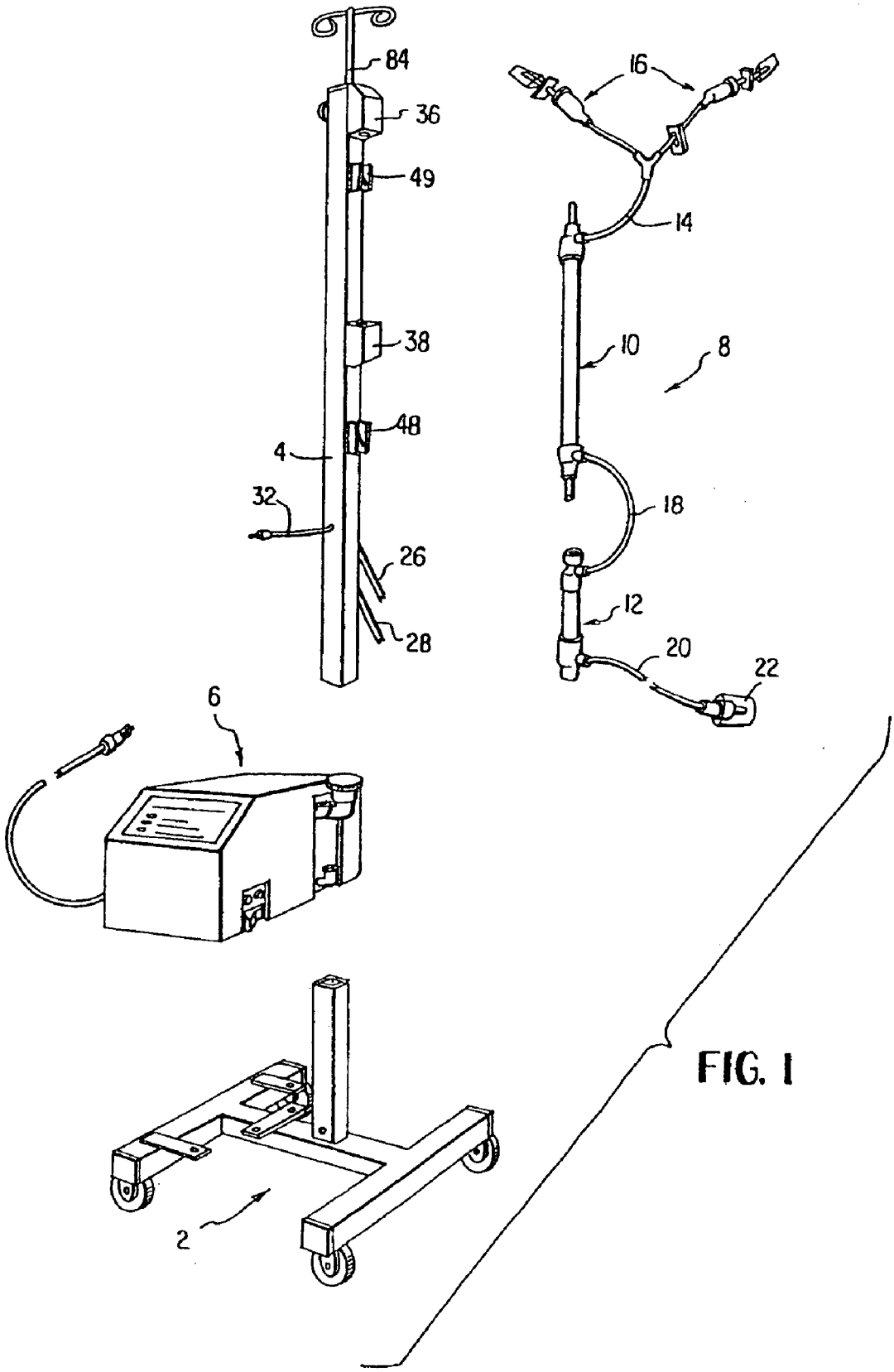
FIG. 1 is an exploded view of the apparatus in accordance with the invention.

FIG. 1 is an exploded view of a preferred embodiment of the invention. A base 2, which preferably has wheels for ease of mobility, supports a pole 4 and a heating unit 6. Pole 4 removably receives a disposable unit 8 which includes a heat exchanger 10 and a filter 12. Tube 14 is in fluid communication with one end of heat exchanger 10 and connects it to a pair of bags spikes 16. The bag spikes are known in the art and are used to puncture and allow the dispensing of a body fluid from a storage bag. Tube 18 connects a lower end of heat exchanger 10 to an upper end of filter 12 and tube 20 connects a lower end of filter 12 to cannula 22 to allow fluids to be introduced into a patient. As will be more fully described below, the entire unit 8 is manufactured of an inexpensive material and is disposable to ensure sterility.

FIG. 2 is a longitudinal cross-section of pole 4 with heat exchanger 10 partially mounted thereon. Pole 4 includes a housing 24 which is attached to base 2 (FIG. 1) to extend substantially vertically. Housing 24 is preferably a hollow square tube, and hoses 26 and 28 extend along a hollow portion of housing 24. Preferably, hoses 26 and 28 exit housing 24 via opening 30. In addition, electric conductor 32 extends along the hollow portion of housing 24 and exits by way of a second opening 34.

Figure 4:
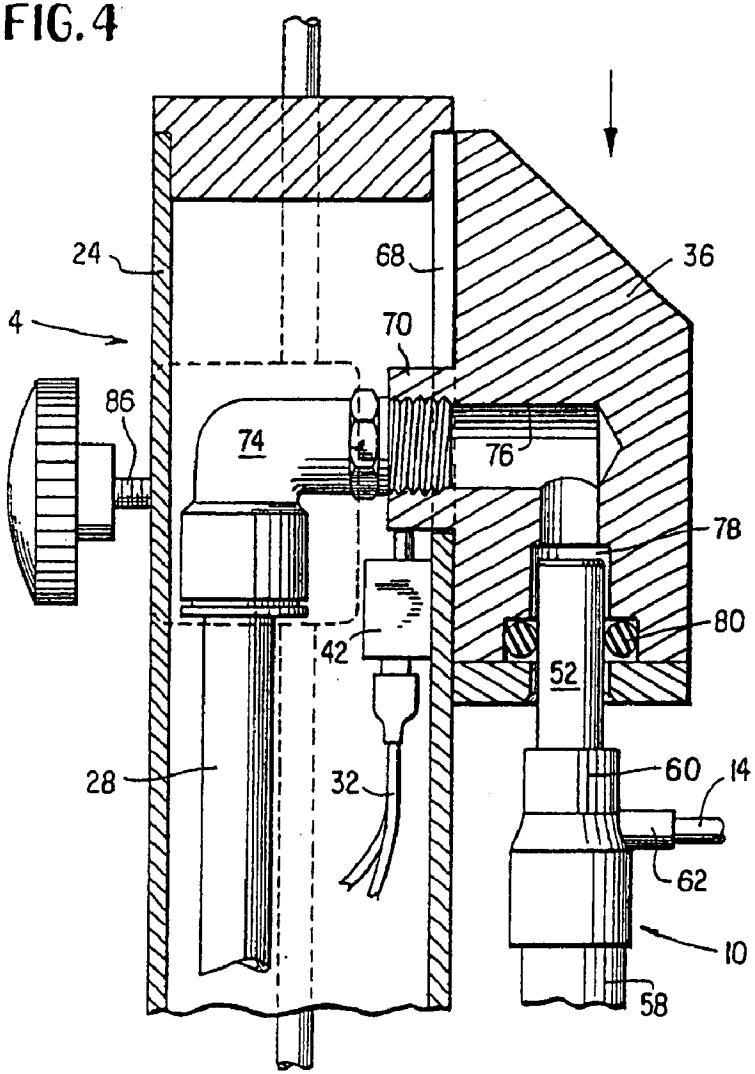
FIG. 4 is an enlarged cross-section of an upper end of the support pole.

Heat exchanger 10 is removably received by first detachable fluid connector 36 and second detachable fluid connector 38. The structure of fluid connectors 36 and 38 will be more fully described with respect to FIGS. 4 and 5. Detachable fluid connector 36 is mounted for vertical movement with respect to housing 24 to allow heat exchanger 10 to be easily attached to pole 4 and detached. Accordion element 40 is placed in hose 28 to permit fluid connector 36 to move vertically. Sensor 42 detects when fluid connector 36 is in its lowermost position (as shown in FIG. 4), sensor 44 detects when heat exchanger 10 is in an operable position, and sensor 46 detects when filter 12 is in operable position.

Filter 12 is supported on pole 4 by U-shaped bracket 48. The distance between the legs of the bracket is slightly less than the diameter of the filter so that it "snaps" into place. Similarly, a U-shaped bracket 49 is located between connectors 36 and 38. Bracket 49 holds heat exchanger 10 aligned with connector 36 during insertion of the heat exchanger.

FIG. 3 is a longitudinal cross-section of heat exchanger 10. An inner tube 50 has ends 52 and 54 which are adapted to be received in respective fluid connectors 36 and 38. A central portion 56 of tube 50 is helically shaped to provide a helical groove on the exterior of tube 50. Tube 50 is preferably made of aluminum, and the helical surface is produced by twisting the tube.

An outer tube 58 fits over the inner tube 50 in a central portion thereof The space between the helical central portion 56 and the outer tube 58 forms a helical path extending between opposite ends of outer tube 58.

An inlet connector 60 is secured to one end of outer tube 58 and includes connection 62 which receives tube 14 (see FIG. 2). End 52 of inner tube 50 extends beyond the upper edge of inlet connector 60 to provide a nipple for engagement with fluid connectors 36 as will be more fully described with respect to FIG. 4.

Outlet connector 64 is secured to a second end of outer tube 58, provides connection 66 for attachment to tube 18, and allows end 54 to project to form a nipple for being received in fluid connector 38.

FIG. 4 is an enlarged cross section of an upper end of pole 4. Housing 24 has a slot 68 in one side thereof for receiving a projection 70 from fluid connector 36. Projection 70 has outwardly extending ears 72 (see FIG. 5) to secure the fluid connector to the pole and yet to allow it to move in the direction indicated by the arrow in FIG. 4.

Elbow 74 is threadedly connected to projection 70 to connect hose 28 with inner passage 76. Recess 78 connects with passage 76 and receives nipple end 52 of heat exchanger 10. O-ring seal 80 is received in an enlarged portion of recess 78 to provide a fluid-tight seal. It will be appreciated that fluid passing through hose 28 is thus connected to inner tube 50 of heat exchanger 10.

Figure 5:
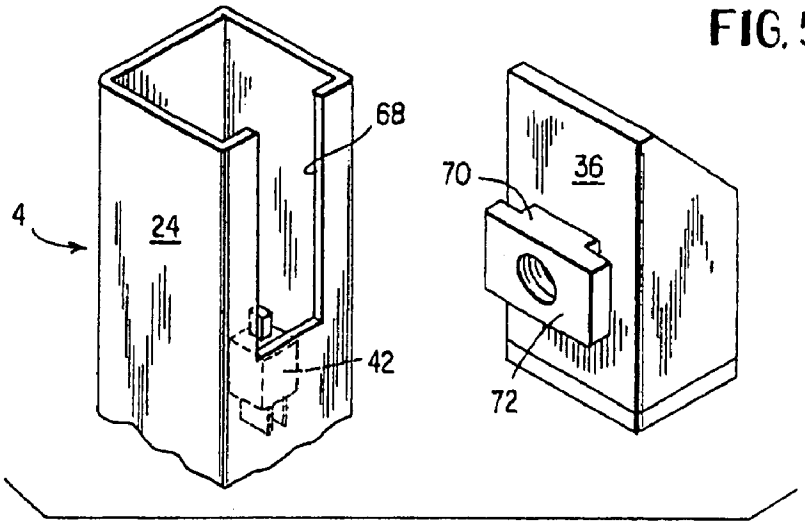
FIG. 5 is an exploded perspective of a movable mounting block and the upper end of the support pole.

FIG. 5 is an exploded view of the fluid connector 36 and the upper portion of housing 24.

Fluid connector 38 is similar to fluid connector 36, except that connector 38 is secured to housing 24.

It will be appreciated that heat exchanger 10 may be easily attached to pole 4 by inserting end 54 into fluid connector 38 and by lowering fluid connector 36 onto end [52] *52*. When this is accomplished, heat exchanger 10 will be supported mainly by fluid connectors 36 and 38.

Figure 6:
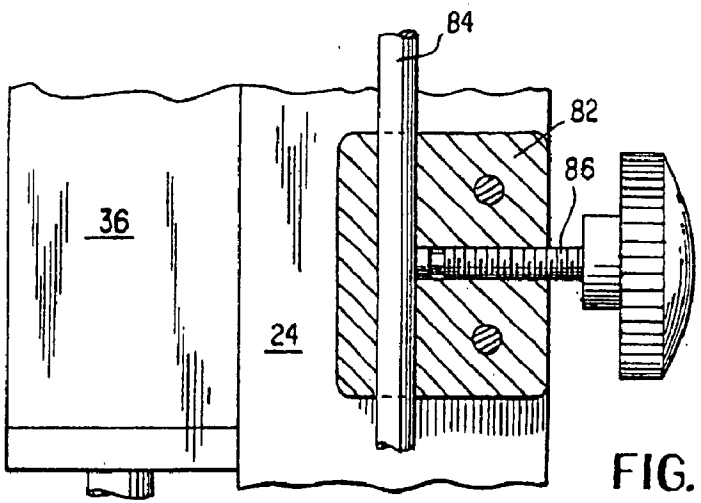
FIG. 6 is a side view of the upper end of the support pole shown in FIG. 4.

FIG. 6 is a side view of the top portion of pole 4 with a bracket 82 shown in cross-section. Bracket 82 has a hole therethrough for supporting a rod 84 which in turn supports bags containing fluids to be administered to a patient. A threaded stem 86 engages rod 84 to allow rod 84 to be adjusted in height.

Figure 7:
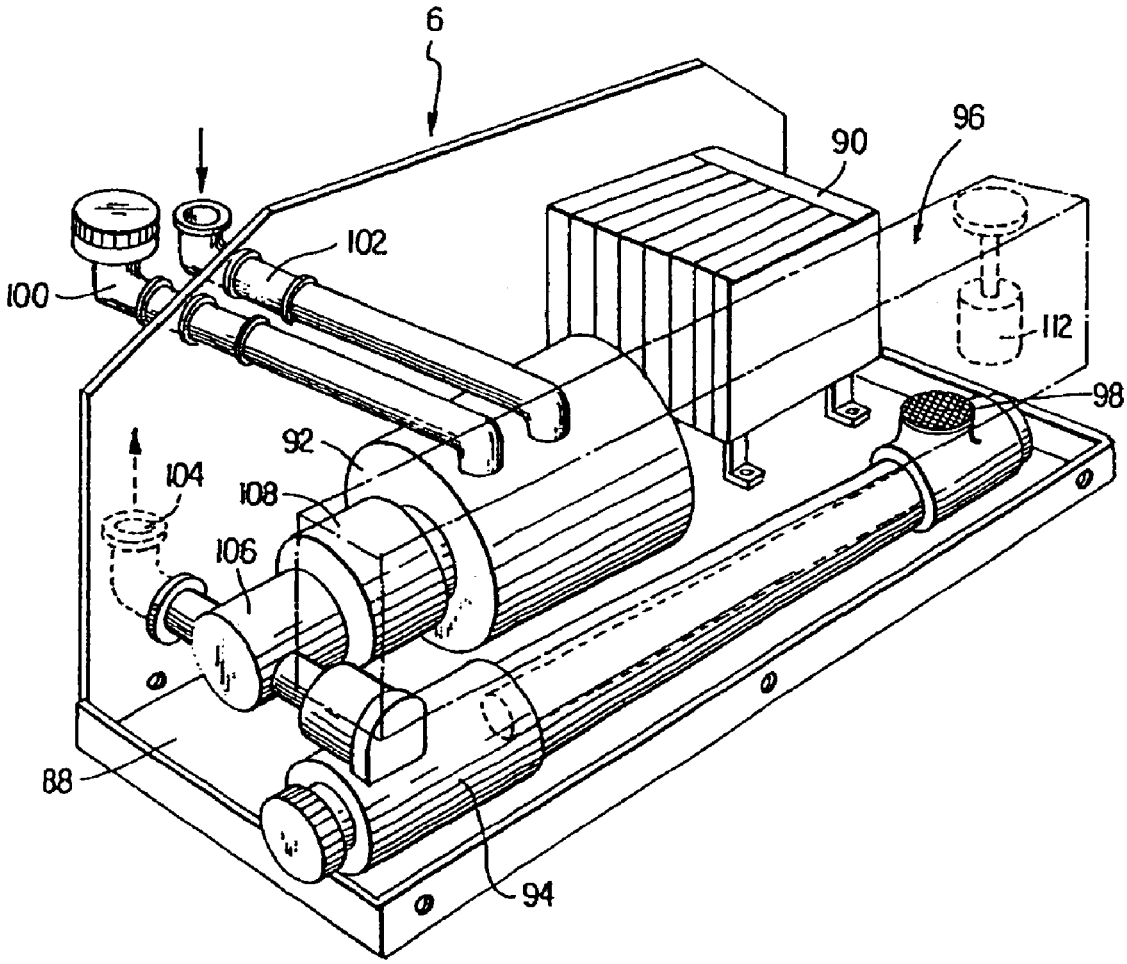
FIG. 7 is a perspective view of the heating element with the cover removed and the storage tank shown in phantom lines.
Figure 8:
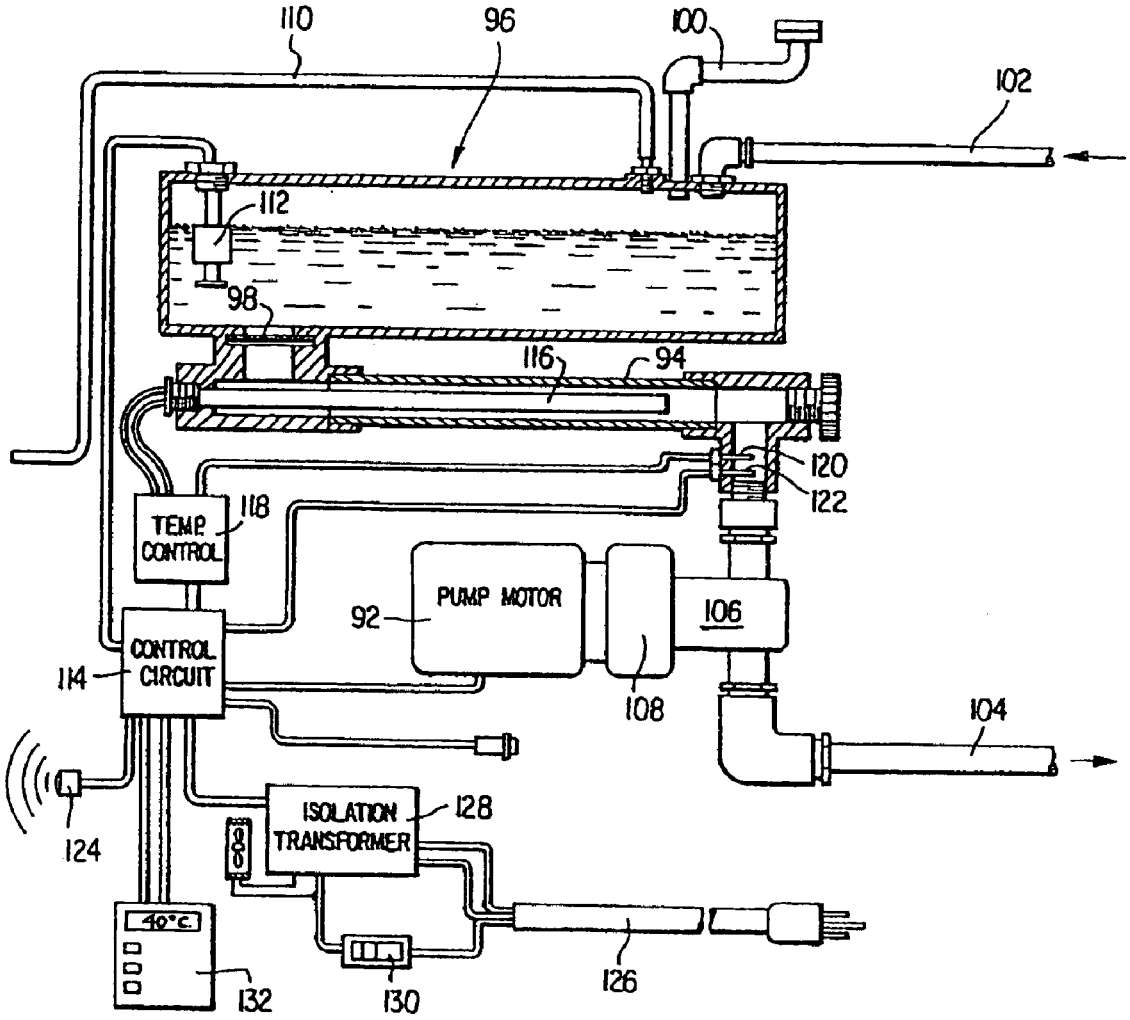
FIG. 8 is a schematic view showing the preferred fluid circuit.

FIG. 7 is a perspective view of heating unit 6, with a cover removed. FIG. 8 is a schematic flow diagram of the unit shown in FIG. 7 and these two Figures will be discussed together.

A base 88 supports electrical components 90, a pump motor 92, and a heater 94. A tank 96 sits on top of heater 94, and filter 98 is located between an outlet of the tank and an inlet of the heater. A fill port 100 is connected to the top of tank 96 to allow circulating fluid to be introduced into the system. Inlet 102 also connects to the top of tank 96 and receives circulating fluid from either hose 26 or 28, and outlet 104 supplies heated fluid to hose 28 or 26.

The warming fluid is driven through the heat exchanger circuit by pump 106 which is connected to the pump motor by magnetic clutch 108.

With particular reference to FIG. 8, tank 96 includes an air vent and overflow tube 110, and a float switch 112. The float switch is in turn connected to a control circuit 114 to permit operation of the device only when sufficient fluid is present. Heater 94 comprises a tubular channel having an electric heating rod 116 therein, and the heating rod is connected to a temperature control circuit 118 which is in turn also connected to control circuit 114. As fluid flows from tank 96 through filter 98 and through heater 94, it is warmed, and the temperature is measured by temperature probe 120, [_] which is located in the outlet of heater 94. Temperature control probe 120 is connected to temperature control circuit 118 to control energization of heating rod 116. A second temperature control probe 122 is also located in the outlet of heater 94 and is connected to control circuit 114 to ensure that the temperature does not exceed a predetermined level. If the temperature of the warming fluid is too high, the blood cells could be destroyed, and it is thus important either to automatically shut down the heating system or to activate an alarm such as that shown at 124.

Power is provided through power cord 126, and the voltage is adjusted by an isolation transformer 128. A switch 130 activates the entire electrical system, and the operation of the system, including the fluid temperature is displayed on panel 132.

In operation of the apparatus is accordance with the invention, the unit is rolled to a location adjacent to a patient, and a sterile unit 8 is installed between fluid connectors 36 and 38. Cannula 22 is attached to the patient, and bag spikes 16 are inserted into appropriate bags containing the desired fluid to be administered to the patient. Switch 130 is be warmed by the heat exchanger. If filter 12 has been placed in the circuit, the warmed body fluid then passes through the filter and into the patient. If filter 12 is not being used, tube 18 is connected directly to the cannula 22 for direct admission of the warm body fluid to the patient.

It will be appreciated that a unique self-contained unit has been described which provides sterility by use of an easily-installed disposable heat exchanger circuit. Modifications within the scope of the appended claims will be apparent to those who are skilled in the art.

What is claimed is:

1. In combination first and second fluid connector means for removably receiving respective first and second warming fluid ports of a heat exchanger *and for facilitating passage of a warming fluid*, and support means for supporting *said* first and second fluid connector means, each of said fluid connector means comprising a passageway for passing said warming fluid and means for engaging a respective said first or second warming fluid port to allow said warming fluid in said passageway to communicate with said port and to physically support said heat exchanger in cooperation with the other of said fluid connector means, fluid circulation means for circulating said warming fluid to said first and second fluid connector means, and temperature control means for controlling the temperature of said warming fluid, wherein one of said first and second fluid connector means is movably mounted to said support means for movement with respect to said support means between at least first and second positions, [wherein] *such that* said first and second fluid connector means [are spaced by a first distance for engaging] *engage* said warming fluid ports when said one of said fluid connectors is in said first position and [are spaced by a second distance for releasing] *release* said warming fluid ports when said one of said fluid connectors is in said second position,

*wherein each of said means for engaging comprises means for removably receiving or releasing one of said warming fluid ports in a single mechanical action.*

2. A combination according to claim 1 wherein said means for [engaging] *removably receiving or releasing* comprises means forming a recess for receiving a said fluid port.

3. A combination according to claim 2 wherein said recess includes seal means for preventing leakage of said warming fluid.

4. A combination according to claim 3 wherein said seal is an O-ring seal.

5. A combination according to claim 1 wherein said support means is elongated in a first direction, said one of said first and second connector means is mounted to said support means for linear movement in said direction toward or away from the other of said first and second connector means between said first and second positions, and said other of said first and second connector means is fixed with respect to said support means.

6. A combination according to claim 5 wherein said means for engaging comprises a cylindrical recess and wherein said cylindrical recess of said first fluid connector means is axially aligned with said cylindrical recess of said second fluid connector means.

7. A combination according to claim 2 wherein a longitudinal axis of said recess of said first fluid connector means is parallel to a longitudinal axis of said recess of said second fluid connector means, and said first fluid connector means is mounted for linear movement in the direction of said longitudinal axis.

8. A combination according to claim 7 further comprising said heat exchanger, wherein said heat exchanger comprises a central tube and an outer tube having a length shorter than that of said central tube wherein said first and second warming fluid ports comprise portions of said central tube which extend beyond respective ends of said outer tube and said central and outer tubes form a passageway for a fluid to be warmed.

9. A combination according to claim 8 wherein said heat exchanger further comprises first and second end caps, each of said first and second end caps having a first part sealingly secured to an outer surface of a respective end of said outer tube and a second part extending away from said first part and sealingly engaged to a side of said central tube.

10. A combination according to claim 9 wherein said second portion of said cap means comprises an open cylinder in contact with said side of said central tube.

11. A combination according to claim 8 wherein said temperature control means comprises heater means in fluid communication with said warming fluid ports.

12. A combination according to claim 11 wherein said heater means comprises an electrical fluid heating element, a storage tank containing said first *warming* fluid, and pump means for circulating said first *warming* fluid in a circuit including said heating element, said tank, and said central tube of said heat exchanger.

13. A combination according to claim 12 wherein said heater means and said support means are mounted on a common wheeled base and further comprising switch means for detecting when said heat exchanger is operatively mounted on said support means.

14. A combination according to claim 13 further comprising filter means in fluid communication with said fluid to be warmed.

[15. A sterile heat exchange for controlling the temperature of a physiological fluid comprising a central tube having high heat conductivity for carrying a temperature-controlled fluid, an outer tube shorter than said central tube and surrounding a part of said central tube to form a passageway for said physiological fluid between said central and outer tubes, and first and second end caps, each of said end caps having a first part extending axially along an outer surface of said outer tube and being sealed and secured to said outer surface and a second part sealingly engaging said central tube to ensure maintenance of sterility during operation, said second part comprising an elongate cylindrical opening engaging an outer surface of said central tube and extending away from said first part and wherein said inner tube extends beyond each of said second parts and forms two elongate connections for being slidingly received in an elongate recess.]

16. A heat exchanger according to claim [15] *19* wherein said central tube is of aluminum.

17. A heat exchanger according to claim [15] *19* wherein said central tube has an exterior surface providing increased surface area.

18. A heat exchanger according to claim 17 wherein said exterior surface is helical and a longitudinal axis of said central tube is straight.

19. [A heat exchanger according to claim 15] *A sterile heat exchanger for controlling the temperature of a physiological fluid comprising a central tube having high heat conductivity for carrying a temperature-controlled fluid, an outer tube shorter than said central tube and surrounding a part of said central tube to form a passageway for said physiological fluid between said central and outer tubes, and first and second end caps, each of said end caps having a first part extending axially along an outer surface of said outer tube and being sealed and secured to said outer surface and a second part sealingly engaging said central tube to ensure maintenance of sterility during operation, said second part comprising an elongate cylindrical opening engaging an outer surface of said central tube and extending away from said first part and wherein said inner tube extends beyond each of said second parts and forms two elongate connections for being slidingly received in an elongate recess,* wherein each of said end caps includes a port for communicating a fluid to be warmed with said passageway.

*20. In combination*

*first and second fluid connector means for removably receiving respective first and second warming fluid ports of a heat exchanger for receiving a warming fluid, and support means for supporting said first and second fluid connector means,*

*each of said fluid connector means comprising a passageway for passing said warming fluid and means for engaging a respective said first or second warming fluid port to allow said warming fluid in said passageway to communicate with said port and to physically support said heat exchanger in cooperation with the other of said fluid connector means,*

*fluid circulation means for circulating said warming fluid to said first and second fluid connector means, and*

*temperature control means for controlling the temperature of said warming fluid,*

*wherein one of said first and second fluid connector means is movably mounted to said support means for movement with respect to said support means between at least first and second positions, such that said first and second fluid connector means are spaced by a first distance for engaging said warming fluid ports when said one of said fluid connectors is in said first position and are spaced by a second distance for releasing said warming fluid ports when said one of said fluid connectors is in said second position, said means for engaging comprises means forming a recess for receiving a said fluid port, said recess includes an O-ring seal for preventing leakage of said warming fluid, and wherein said support means is elongated in a first direction, said one of said first and second connector means is mounted to said support means for linear movement in said direction toward or away from the other of said first and second connector means between said first and second positions, and said other of said first and second connector means is fixed with respect to said support means.*

*21. A combination according to claim 20 wherein said means for engaging comprises a cylindrical recess and wherein said cylindrical recess of said first fluid connector means is axially aligned with said cylindrical recess of said second fluid connector means.*

* * * * *